US010479761B2

(12) United States Patent
Davison et al.

(10) Patent No.: US 10,479,761 B2
(45) Date of Patent: Nov. 19, 2019

(54) PROCESS FOR THE PRODUCTION OF FORMALDEHYDE-STABILIZED UREA

(71) Applicant: JOHNSON MATTHEY PUBLIC LIMITED COMPANY, London (GB)

(72) Inventors: Thomas Davison, Billingham (GB); John David Pach, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/344,610

(22) PCT Filed: Oct. 3, 2017

(86) PCT No.: PCT/GB2017/052965
§ 371 (c)(1),
(2) Date: Apr. 24, 2019

(87) PCT Pub. No.: WO2018/078318
PCT Pub. Date: May 3, 2018

(65) Prior Publication Data
US 2019/0263753 A1  Aug. 29, 2019

(30) Foreign Application Priority Data
Oct. 26, 2016  (GB) .................................. 1618121.6

(51) Int. Cl.
C07C 273/02 (2006.01)
C07C 273/04 (2006.01)
(Continued)

(52) U.S. Cl.
CPC ............ *C07C 273/025* (2013.01); *C01B 3/02* (2013.01); *C01C 1/0405* (2013.01);
(Continued)

(58) Field of Classification Search
CPC ........... C01B 3/382; C01B 3/025; C01B 3/48; C01B 3/52; C01B 3/56; C01B 2203/0283;
(Continued)

(56) References Cited

U.S. PATENT DOCUMENTS

2018/0072658 A1* 3/2018 Erlandsson ............. C01B 3/025
2018/0072659 A1* 3/2018 Erlandsson ......... C07C 29/1518
(Continued)

FOREIGN PATENT DOCUMENTS

WO    WO2016/132091        8/2016
WO    WO2016/132092 A1     8/2016

OTHER PUBLICATIONS

Holdor Topsoe, "Integration of Urea-Formaldehyde Production,, Boosting Profitability for Urea Producers," 6th GPCA Fertilizer Conveniton, Dubai, Sep. 14-16, 2015, Available from http://gpcafertilizers.com/2015/wp-cotent/uploads/2015/10/Haldor-Topsoe-David-James-Bray.pdf.
(Continued)

Primary Examiner — Jafar F Parsa
(74) Attorney, Agent, or Firm — BakerHostetler

(57) ABSTRACT

An integrated process for the production of a formaldehyde-stabilised urea is described comprising the steps of: (a) generating a synthesis gas comprising hydrogen, nitrogen, carbon monoxide, carbon dioxide and steam in a synthesis gas generation unit; (b) dividing the synthesis gas into a first synthesis gas stream and a smaller second synthesis gas stream; (c) subjecting the first synthesis gas stream to one or more stages of water-gas shift in one or more water-gas shift reactors to form a shifted gas; (d) cooling the shifted gas to below the dew point and recovering condensate to form a dried shifted gas; (e) recovering carbon dioxide from the dried shifted gas in a carbon dioxide removal unit to form a carbon dioxide-depleted synthesis gas; (f) subjecting the
(Continued)

carbon dioxide-depleted synthesis gas to a stage of methanation in one or more methanation reactors to form an ammonia synthesis gas; (g) synthesising ammonia from the ammonia synthesis gas in an ammonia production unit and recovering the ammonia; (h) reacting a portion of the ammonia and at least a portion of the recovered carbon dioxide stream in a urea production unit to form a urea stream; and (i) stabilising the urea by mixing the urea stream and a stabiliser prepared using formaldehyde to form a stabilised urea, wherein the formaldehyde is generated by steps comprising; (1) passing the second portion of synthesis gas through a scrubber to remove contaminants therefrom and form a scrubbed synthesis gas; (2) synthesising methanol from the scrubbed synthesis gas in a methanol synthesis unit, and recovering the methanol and a methanol synthesis off-gas; (3) combining the methanol synthesis off-gas with the shifted gas and (4) subjecting at least a portion of the recovered methanol to oxidation with air in a formaldehyde stabiliser production unit to produce formaldehyde.

20 Claims, 1 Drawing Sheet

(51) Int. Cl.
*C07C 273/16* (2006.01)
*C07C 31/04* (2006.01)
*C01C 1/04* (2006.01)
*C01B 3/02* (2006.01)
*C07C 29/151* (2006.01)

(52) U.S. Cl.
CPC .......... *C07C 29/1518* (2013.01); *C07C 31/04* (2013.01); *C07C 273/04* (2013.01); *C07C 273/16* (2013.01); *C01B 2203/0283* (2013.01); *C01B 2203/04* (2013.01); *C01B 2203/1223* (2013.01)

(58) Field of Classification Search
CPC ...... C01B 2203/145; C01B 2203/0415; C01B 2203/061; C01B 2203/42; C01B 2203/025; C01B 2203/0244; C01B 2203/043; C01B 2203/062; C01C 1/0488; C07C 45/29; C07C 273/14; C07C 273/10; C07C 273/04; C07C 29/1518; C10G 2/32
See application file for complete search history.

(56) References Cited

U.S. PATENT DOCUMENTS

2018/0362453 A1* 12/2018 Erlandsson ............. C01B 3/382
2019/0031604 A1* 1/2019 Erlandsson ............. C07C 45/29

OTHER PUBLICATIONS

GB1618121.6, Search Report under Section 17(5), dated Aug. 4, 2017.
GB1716139,9, Combined Search and Examination Report under Sections 17 and 18(3) dated Jun. 15, 2018.
WO2018/078318 (PCT/GB2017/052965), International Search Report dated Jan. 4, 2018.
WO2018/078318 (PCT/GB2017/052965), Written Opinion dated Jan. 4, 2018.

* cited by examiner

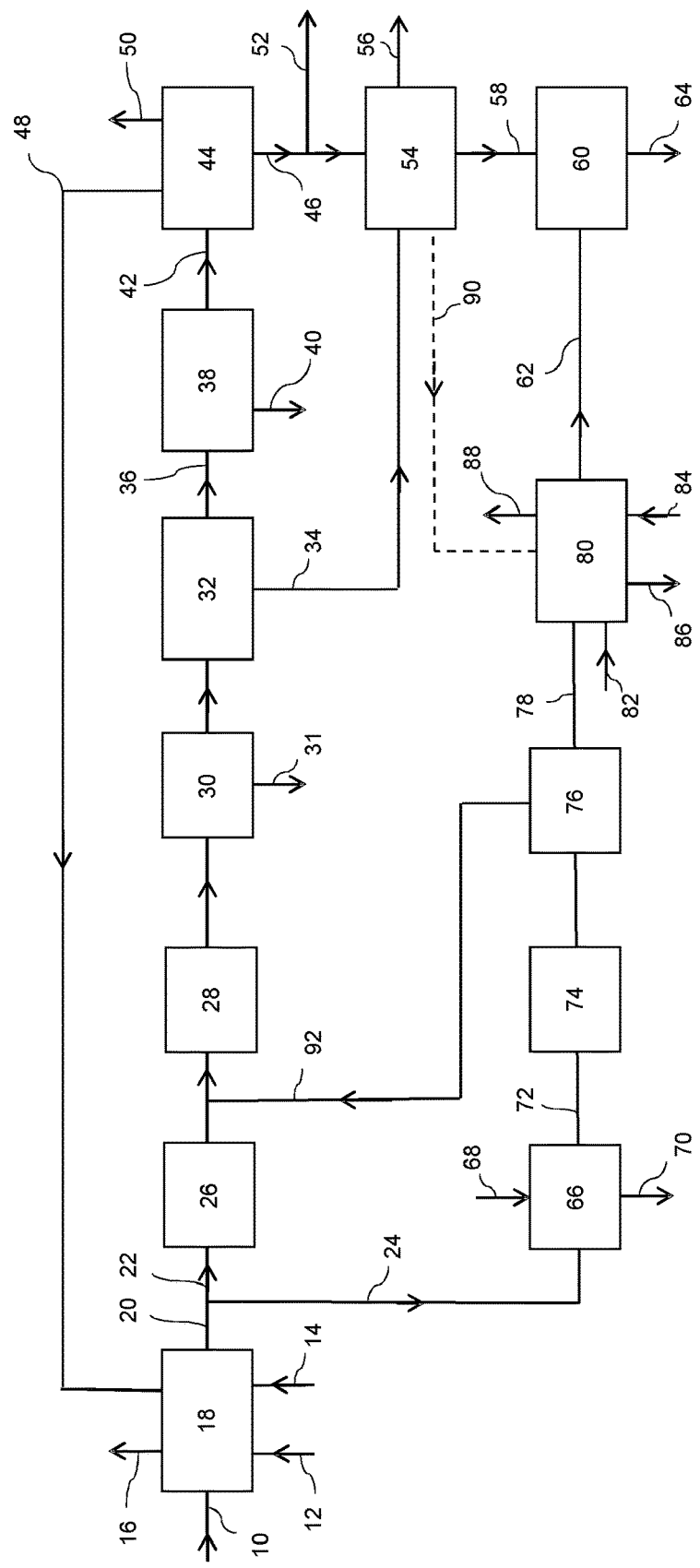

PROCESS FOR THE PRODUCTION OF FORMALDEHYDE-STABILIZED UREA

CROSS-REFERENCE TO RELATED APPLICATIONS

This application is the National Stage of International Patent Application No. PCT/GB2017/052965, filed Oct. 3, 2017, which claims priority to Great Britain Patent Application No. 1618121.6, filed Oct. 26, 2016, the entire disclosures of which applications are incorporated herein by reference for any and all purposes.

The present invention relates to a process for the production of formaldehyde-stabilised urea. More particularly, it relates to an integrated process for the production of formaldehyde-stabilised urea in a process including the co-production of methanol and ammonia.

Urea finds widespread use as a fertiliser and in industrial chemical manufacture. It is conventionally made by reacting ammonia with carbon dioxide to form a solid product which is often shaped by prilling or granulating. Formaldehyde or a urea-formaldehyde concentrate (UFC) are often used to stabilise the urea before or during the shaping process.

However, the demand for formaldehyde to stabilise urea from a single production facility is small and so normally beyond the economic feasibility for a dedicated formaldehyde stabiliser production facility. Due to the small scale of the requirements, the formaldehyde is normally produced at a separate dedicated formaldehyde stabiliser production facility and transported to the ammonia/urea production facility where it is stored.

WO2016/132092 and WO2016/132091 disclose integrated processes for the production of formaldehyde-stabilised urea in which methanol used in formaldehyde production is synthesised from a carbon dioxide-depleted synthesis gas recovered from a carbon-dioxide removal unit.

We have developed an integrated urea-formaldehyde process with a dedicated formaldehyde stabiliser production unit based on a methanol-ammonia co-production process that offers a lower pressure drop, reduced risk of catalyst poisoning in the methanol synthesis unit and the formaldehyde stabiliser production unit and provides flexibility in the amount of methanol, ammonia and urea synthesised.

Accordingly, the invention provides a process for the production of formaldehyde-stabilised urea comprising the steps of: (a) generating a synthesis gas comprising hydrogen, nitrogen, carbon monoxide, carbon dioxide and steam in a synthesis gas generation unit; (b) dividing the synthesis gas into a first synthesis gas stream and a smaller second synthesis gas stream; (c) subjecting the first synthesis gas stream to one or more stages of water-gas shift in one or more water-gas shift reactors to form a shifted gas; (d) cooling the shifted gas to below the dew point and recovering condensate to form a dried shifted gas; (e) recovering carbon dioxide from the dried shifted gas in a carbon dioxide removal unit to form a carbon dioxide-depleted synthesis gas; (f) subjecting the carbon dioxide-depleted synthesis gas to a stage of methanation in one or more methanation reactors to form an ammonia synthesis gas; (g) synthesising ammonia from the ammonia synthesis gas in an ammonia production unit and recovering the ammonia; (h) reacting a portion of the ammonia and at least a portion of the recovered carbon dioxide stream in a urea production unit to form a urea stream; and (i) stabilising the urea by mixing the urea stream and a stabiliser prepared using formaldehyde to form a stabilised urea, wherein the formaldehyde is generated by steps comprising: (1) passing the second portion of synthesis gas through a scrubber to remove contaminants therefrom and form a scrubbed synthesis gas; (2) synthesising methanol from the scrubbed synthesis gas in a methanol synthesis unit, and recovering the methanol and a methanol synthesis off-gas; (3) combining the methanol synthesis off-gas with the shifted gas and (4) subjecting at least a portion of the recovered methanol to oxidation with air in a formaldehyde stabiliser production unit to produce formaldehyde.

In the claimed process, a parallel methanol and formaldehyde synthesis process is used which reduces the pressure drop across the ammonia plant. This enables the ammonia production to be maximised. The inclusion of a scrubber allows contaminants present in the synthesis gas, such as ammonia and any amine compounds that may harm the methanol oxidation catalyst in the formaldehyde stabiliser production unit to be removed. Control of the portion of the second synthesis gas stream used in the methanol synthesis provides flexibility in the amount of methanol and formaldehyde that may be synthesised.

The synthesis gas, comprising carbon monoxide, carbon dioxide, hydrogen and nitrogen provided in step (a) may be formed by any suitable means. Different synthesis gas generation units can provide synthesis gases with different carbon monoxide:carbon dioxide ratios. The process allows the product mix to be adjusted for a wide range of synthesis gas compositions. The synthesis gas generation may comprise primary steam reforming of a preferably desulphurised hydrocarbon, such as natural gas, naphtha or a refinery off-gas, and secondary reforming with air or oxygen-enriched air; or by the gasification of a carbonaceous feedstock, such as coal or biomass with air. Preferably the synthesis gas generation stage comprises steam reforming a hydrocarbon. This may be achieved by primary reforming a hydrocarbon with steam in externally-heated catalyst-filled tubes in a fired- and/or gas-heated steam reformer and secondary reforming the primary-reformed gas mixture in an autothermal or secondary reformer by subjecting it to partial combustion with air, or air enriched in oxygen, and then passing the partially combusted gas mixture through a bed of steam reforming catalyst. A heat exchange reformer, such as a gas-heated steam reformer (GHR), may be operated in parallel with a conventional fired reformer or in series with a conventional fired reformer and the product gas fed to a common secondary reformer. By-passing a portion of the hydrocarbon feedstock around a primary reformer may be used to reduce the carbon monoxide:carbon dioxide ratio in the synthesis gas. If desired one or more stages of adiabatic pre-reforming may also be performed before the fired reformer and/or heat exchange reformer.

The primary reforming catalyst typically comprises nickel at levels in the range 5-30% wt, supported on shaped refractory oxides, such as alpha alumina, magnesium aluminate or calcium aluminate. If desired, catalysts with different nickel contents may be used in different parts of the tubes, for example catalysts with nickel contents in the range 5-15% wt or 30-85% wt may be used advantageously at inlet or exit portions of the tubes. Alternatively, structured catalysts, wherein a nickel or precious metal catalyst is provided as a coated layer on a formed metal or ceramic structure may be used, or the catalysts may be provided in a plurality of containers disposed within the tubes. Steam reforming reactions take place in the tubes over the steam reforming catalyst at temperatures above 350° C. and typically the process fluid exiting the tubes is at a temperature in the range 650-950° C. The heat exchange medium flowing around the outside of the tubes may have a temperature in the range 800-1300° C. In a GHR the catalyst at temperatures again are above 350° C. and typically the process fluid exiting the tubes is at a temperature in the range 500-950° C. and the heat exchange medium flowing around the outside of the tubes may have a temperature in the range 500-1200° C. The pressure may be in the range 10-80 bar abs. In a secondary reformer, the primary-reformed gas is partially combusted often in a burner apparatus mounted usually near the top of the reformer. The partially combusted reformed gas is then passed adiabatically through a bed of a steam reforming catalyst usually disposed below the burner apparatus, to bring the gas composition towards equilibrium. Heat for the endothermic steam reforming reaction is supplied by the hot, partially combusted reformed gas. As the partially combusted reformed gas contacts the steam reforming catalyst it is cooled by the endothermic steam reforming reaction to temperatures in the range 800-1100° C. The bed of steam reforming catalyst in the secondary reformer typically comprises nickel at levels in the range 5-30% wt, supported on shaped refractory oxides, but layered beds may be used wherein the uppermost catalyst layer comprises a precious metal, such as platinum or rhodium, on a zirconia support. Such steam reforming apparatus and catalysts are commercially available.

Alternatively, the steam reforming may be achieved by passing a mixture of the hydrocarbon and steam through an adiabatic pre-reformer containing a bed of steam reforming catalyst and then passing the pre-reformed gas mixture and air to an autothermal reformer which operates in the same way as the secondary reformer to produce a gas stream containing hydrogen, carbon oxides and steam. In adiabatic pre-reforming, a mixture of hydrocarbon and steam, typically at a steam to carbon ratio in the range 1-4, is passed at an inlet temperature in the range 300-620° C. to a fixed bed of pelleted nickel-containing pre-reforming catalyst. Such catalysts typically comprise 40% wt nickel (expressed as NiO) and may be prepared by co-precipitation of a nickel-containing material with alumina and promoter compounds such as silica and magnesia. Again, the pressure may be in the range 10-80 bar abs.

Alternatively, the synthesis gas reaction stream may be formed by gasification of coal, biomass or other carbonaceous material with air using gasification apparatus. In such processes the coal, biomass or other carbonaceous material is heated to high temperatures in the absence of a catalyst to form a crude synthesis gas often containing sulphur contaminants such as hydrogen sulphide, which have to be removed. Gasification of carbonaceous feedstock to produce a synthesis gas may be achieved using known fixed bed, fluidised-bed or entrained-flow gasifiers at temperatures in the range 900-1700° C. and pressures up to 90 bar abs. The crude synthesis gas streams require additional treatments known in the art to remove unwanted sulphur and other contaminants.

In a preferred process, the synthesis gas generation stage comprises primary reforming a hydrocarbon, particularly natural gas, in a fired steam reformer to produce a gas stream comprising hydrogen, carbon monoxide, carbon dioxide and steam, and secondary reforming in which the primary reformed gas is further reformed in a secondary reformer using air or oxygen-enriched air to provide a synthesis gas stream comprising hydrogen, carbon oxides and nitrogen.

In the present invention, the synthesis gas is divided in step (b) into a first synthesis gas stream and a second synthesis gas stream. The first synthesis gas stream is used to synthesise urea and the second synthesis gas stream is used to synthesise formaldehyde. The amount of synthesis gas separated to form the second synthesis gas stream may be 0.25 to 30% by volume, preferably 0.25 to 20% by volume, more preferably 0.25 to 10% by volume of the synthesis gas. Where the synthesis gas is generated by primary and secondary reforming, a portion of the primary reformed gas and/or the secondary reformed gas may be separated to form the second synthesis gas stream. The amount of primary reformed gas and/or secondary reformed gas separated to form the second synthesis gas stream is relatively small compared to the volume of synthesis gas generated in the synthesis gas generation unit. Because a primary reformed gas contains higher levels of methane, which is a useful source of hydrogen for ammonia production, it is preferred that the second synthesis gas stream consists of a portion of a secondary reformed gas.

If desired, one air feed may be provided for both the production of the synthesis gas and the production of the formaldehyde. This offers benefits in the reduction of capital and operating costs when compared to that required for the separate systems utilised in the prior art. Thus, a single source of air may be compressed, divided into first and second portions, the first portion provided to a formaldehyde stabiliser production unit and the second portion further compressed and provided to a synthesis gas generation unit. The first portion may be compressed to a pressure in the range 1.1-5 bar abs. The second portion of compressed air fed to the synthesis gas generation unit is used to generate the synthesis gas, for example in a secondary or autothermal reformer. The second portion may be compressed to 10-80 bar abs. If desired, the second portion may also be preheated. The amount of air in the second portion may also be varied to control the eventual hydrogen:nitrogen ratio in the ammonia synthesis gas. The proportion of compressed air fed to the formaldehyde stabiliser production unit may be up to about 20% by volume, preferably in the range 1.5-15% by volume, of the total air fed to the process.

Before recovery of the carbon dioxide, the first synthesis gas stream is subjected in step (c) to one or more stages of water-gas shift to produce a shifted synthesis gas with the desired gas composition. In a water-gas shift stage, a portion of the carbon monoxide in the stream is converted to carbon dioxide. Any suitable catalytic shift conversion reactor and catalyst may be used. If insufficient steam is present, steam may be added to the gas stream before it is subjected to the water-gas shift conversion. The reaction may be depicted as follows;

$$H_2O+CO \leftrightarrows H_2+CO_2$$

The reaction may be carried out in one or more stages. The, or each, stage may be the same or different and may be selected from high temperature shift, low temperature shift, medium temperature shift, isothermal shift and sour shift, and is preferably selected from a single stage of high temperature shift, a combination of high temperature shift and low temperature shift, a single stage of medium temperature shift, or a combination of medium temperature shift and low temperature shift.

High temperature shift catalysts may be promoted iron catalysts such as chromia- or alumina-promoted magnetite catalysts. Other high temperature shift catalysts may be used, for example iron/copper/zinc oxide/alumina catalysts, manganese/zinc oxide catalysts or zinc oxide/alumina catalysts. Medium, low temperature and isothermal shift catalysts typically comprise copper, and useful catalysts may comprise varying amounts of copper, zinc oxide and alumina. Alternatively, where sulphur compounds are present in the gas mixture, such as synthesis gas streams obtained by gasification, so-called sour shift catalysts, such as those comprising sulphides of molybdenum and cobalt, are preferred. Such water-gas shift apparatus and catalysts are commercially available.

For high temperature shift catalysts, the temperature in the shift converter may be in the range 300-460° C., for medium temperature shift catalysts the temperature may be in the range 190-300° C. and for low-temperature shift catalysts the temperature may be 185-270° C. For sour shift catalysts the temperature may be in the range 200-370° C. The flow-rate of synthesis gas containing steam may be such that the gas hourly space velocity (GHSV) through the bed of water-gas shift catalyst in the reactor may be 6000 hour$^{-1}$. The pressure may be in the range 10-80 bar abs.

The water-gas shift stage produces a shifted gas. By the term shifted gas we include a partially shifted gas in which the conversion of carbon monoxide to carbon dioxide is incomplete.

In a preferred embodiment, the water-gas shift stage comprises a high temperature shift stage or a medium temperature shift stage or an isothermal shift stage with or without a low temperature shift stage. In a particularly preferred arrangement, the water-gas shift stage comprises a high temperature shift stage to form a partially shifted gas and, following adjustment of the temperature of the partially shifted gas, a low temperature shift stage to form a shifted gas mixture.

Steam present in the shifted gas mixture is condensed in step (d) to form a dried shifted gas, which is fed to the carbon dioxide removal unit. This may be achieved by cooling the shifted gas to below the dew point using one or more heat exchangers fed, for example, with cooling water. The condensate recovered may be fed to a condensate stripping unit or, if desired, be fed to steam generators that produce steam for the synthesis gas generation and/or water-gas shift stages.

A carbon dioxide removal unit is used to recover carbon dioxide from the dried shifted synthesis gas in step (e). It is located downstream of a water-gas shift stage, and upstream of the methanation stage. Any suitable carbon dioxide removal unit may be used. Suitable removal units may function by reactive or chemical absorption, such as those known as aMDEA® or Benfield® units that are based on using regenerable amine or potassium carbonate washes, or by physical absorption, based on using methanol, glycol or another liquid at low temperature, such as Rectisol®, Selexol® units. Carbon dioxide removal may also be performed by means of pressure-swing adsorption (PSA) using suitable solid adsorbent materials. Such carbon dioxide removal apparatus and materials are commercially available. Some or all of the carbon dioxide formed in the synthesis gas may be removed to produce a gas stream comprising mainly hydrogen and nitrogen with low levels of carbon monoxide and/or carbon dioxide. The carbon dioxide removed by the carbon dioxide removal unit may be captured, optionally treated to remove contaminants such as hydrogen, and stored or used for reaction downstream with the ammonia produced to form urea.

In the methanation stage (f), residual carbon monoxide and any carbon dioxide in the carbon dioxide depleted synthesis gas is converted to methane in the methanator. Any suitable arrangement for the methanator may be used. Thus the methanator may be operated adiabatically or isothermally. One or more methanators may be used. A nickel-based methanation catalyst may be used. For example, in a single methanation stage, the gas from the carbon dioxide removal unit may be fed at an inlet temperature in the range 200-400° C., preferably 250-325° C. or 325-375° C., to a fixed bed of pelleted nickel-containing methanation catalyst. Such catalysts are typically pelleted compositions, comprising 20-40% wt nickel. Such methanation apparatus and catalysts are commercially available. The pressure for methanation may be in the range 10-80 bar abs or higher up to 250 bar abs.

Steam is formed as a by-product of methanation. The steam is desirably removed using conventional means, such as cooling, e.g. by heat exchange with cold water, and separation of condensate. An ammonia synthesis gas stream may be recovered from the methanation and drying stage. Such methanation apparatus and catalysts are commercially available.

The methanated gas stream may be fed to the ammonia production unit as the ammonia synthesis gas. However, the hydrogen:nitrogen molar ratio of the methanated gas stream may need to be adjusted, for example by addition of nitrogen from a suitable source, or by removal of nitrogen, to provide the ammonia synthesis gas. The adjustment of the hydrogen:nitrogen molar ratio is to ensure the ammonia synthesis reaction operates efficiently. Nitrogen, if added, may be provided from any source, for example from an air separation unit (ASU) and the adjustment may be performed by direct addition of nitrogen to the methanated gas stream. Nitrogen, if removed, may be removed from the synthesis gas by cryogenic cooling to recover liquid nitrogen or may be achieved using pressure-swing adsorption on a suitable adsorbent. Such cryogenic and pressure-swing absorption apparatus and adsorbents are commercially available. The adjusted gas mixture may then be passed to the ammonia synthesis unit as the ammonia synthesis gas.

Ammonia is synthesised in step (g). The ammonia synthesis gas may be compressed to the ammonia synthesis pressure and passed to an ammonia production unit. The ammonia production unit comprises an ammonia converter containing an ammonia synthesis catalyst. The converter may be operated adiabatically or the catalyst and/or reacted gases may be cooled. One or more beds of catalyst may be used in the converter with optional cooling of the reacted gases between beds. One or more converters may be used in parallel if required. The nitrogen and hydrogen react together over the catalyst to form the ammonia product. Ammonia synthesis catalysts are typically iron based but other ammonia synthesis catalysts may be used. The reactor may operate adiabatically or may be operated isothermally. The catalyst beds may be axial and/or radial flow and one or more beds may be provided within a single converter vessel. The conversion over the catalyst is generally incomplete and so the synthesis gas is typically passed to a loop containing a partially reacted gas mixture recovered from the ammonia converter and the resulting mixture fed to the catalyst. The synthesis gas mixture fed to the loop may have a hydrogen:nitrogen ratio of 2.2-3.2. In the ammonia production unit, the hydrogen/nitrogen mixture may be passed over the ammonia synthesis catalyst at high pressure, e.g. in the range 80-350 bar abs, preferably 150-350 bar abs for large-scale plants, and a temperature in the range 300-540° C., preferably 350-520° C.

A purge gas stream containing methane and hydrogen may be taken from the ammonia synthesis loop and fed to the synthesis gas generation step or used as a fuel.

Compression of the synthesis gas is preferably effected in multiple stages, with a first and a second stage performed before the methanol synthesis to achieve a pressure of e.g. 50-100 barg, preferably 80-100 barg, and a third stage after methanation to achieve a higher pressure, e.g. 150-250 barg, before the ammonia synthesis.

Urea is produced in step (h) by reacting ammonia from step (g) with carbon dioxide recovered from step (e). Typically, only a portion of the ammonia produced in step (g) will be used to produce urea, which is limited by the amount of carbon dioxide recovered in step (e). The excess ammonia may be recovered and used to make nitric acid, ammonium nitrate or ammonia products for sale. Any urea production technology may be used. For example, ammonia and carbon dioxide may be combined in a first reactor in the range 140-200° C. and 120-220 bar abs to form ammonium carbamate as follows;

$$NH_3 + CO_2 \leftrightharpoons NH_2COONH_4$$

The ammonium carbamate is then dehydrated in a further reactor to form urea;

$$NH_2COONH_4 \leftrightharpoons NH_2CONH_2 + H_2O$$

The high pressure favours ammonium carbamate formation and the high temperature favours the dehydration, so the resultant mixture contains all the above components. Unreacted carbamate is therefore generally decomposed back to ammonia and carbon dioxide, which may then be recycled to the reactor. The carbon dioxide readily dissolves in the water from the dehydration, which if recycled supresses the equilibria and so the system may be run with excess ammonia to minimise this recycle. The decomposition and subsequent recycling can be carried out in one or more successive stages at decreasing pressures to minimise the ultimate concentration of ammonium carbamate dissolved in the urea solution. An alternative process arrangement uses the fresh carbon dioxide gas to strip unreacted ammonia and carbon dioxide from the ammonium carbamate and urea solution at the same pressure as the reactor. Further unreacted material is recycled from lower pressure stages as ammonium carbamate solution. Such urea production apparatus is commercially available.

A stabilised urea is produced in step (i) by mixing urea produced in step (h) and a stabiliser prepared using formaldehyde recovered from a formaldehyde stabiliser production unit. The stabiliser may be any formaldehyde-containing stabiliser; including aqueous formaldehyde and an aqueous urea-formaldehyde concentrate (UFC). Aqueous formaldehyde and urea formaldehyde concentrate may be prepared directly in the formaldehyde stabiliser production unit. Formaldehyde, either as a concentrated solution or as a combined solution of urea and formaldehyde may be added to molten urea prior to forming into either prills or granules. This reduces the tendency of the urea to absorb moisture and increases the hardness of the surface of the solid particles, preventing both caking (bonding of adjacent particles) and dusting (abrasion of adjacent particles). This maintains the free flowing nature of the product; prevents loss of material through dust, and enhances the stability during long term storage. If urea is available then it is preferable to use the urea formaldehyde solution as a stable solution with a higher formaldehyde concentration can be produced, which minimises the water being added to the molten urea. Such stabilised urea production apparatus is commercially available.

In the present invention, the formaldehyde used in step (i) is produced from methanol formed from the second synthesis gas stream. The second synthesis gas stream, before it is subjected to methanol synthesis, is scrubbed in a scrubber to remove ammonia and any amine compounds that may be present in the synthesis gas. Such compounds have been found to lower the activity of the methanol oxidation catalysts and may not be removed in the methanol synthesis unit. In addition, the scrubber will remove contaminants in the synthesis gas that may harm the methanol synthesis catalyst, such as chloride compounds. Before the second synthesis gas stream is scrubbed, it is preferably cooled in one or more heat exchangers, which may be fed with water to generate steam. This cooling may if desired cool the gas below the dew point so that steam condenses as water, which may be removed by a separator to provide a dried gas to the scrubber. A step of condensate removal upstream of the scrubber removes some of the contaminants. Alternatively, or in addition, the second synthesis gas stream may be cooled by using it to heat one or more process streams, such as the hydrocarbon feedstock, air or oxygen-enriched air, or the scrubbed second synthesis gas.

The second synthesis gas stream, preferably after cooling, is fed to a scrubber. Any design of scrubber may be used. Typically, a scrubber comprises an elongate vessel mounted vertically to which a scrubbing liquor, typically water, is fed near the top and to which the gas to be scrubbed is fed near the bottom. The gas flows upwards through the vessel and encounters the scrubbing liquor flowing downwards, often through a packed bed of metal or ceramic shapes, which removes the contaminants. The contaminated scrubber liquor may then be sent for treatment and may be re-used. The scrubber is preferably fed with water, which may comprise a demineralised water and/or a purified condensate recovered for example from the shifted and/or methanated synthesis gas streams. The scrubber is operated under temperature and pressure conditions suitable to remove the ammonia and other contaminants.

If desired, a guard bed of a suitable adsorbent material for removing any remaining contaminants may be provided in a guard vessel downstream of the scrubber and upstream of the methanol synthesis unit.

The contaminated scrubber liquor recovered from the scrubber may desirably be combined with the condensate recovered from the shifted gas and the combined stream sent for further processing, such as in a condensate distillation unit, to provide purified water for the scrubber and/or steam for the synthesis gas generation unit, the one or more water gas shift stages or the methanol synthesis unit.

The scrubbed second synthesis gas is preferably heated to a suitable methanol synthesis inlet temperature. This may be achieved using one or more heat exchangers, for example a gas-gas interchanger that recovers heat from the second synthesis gas stream. The scrubbed second synthesis gas may then be fed to the methanol synthesis unit.

Methanol is synthesised from the scrubbed second synthesis gas. The synthesis reactions may be depicted as follows:

$$3H_2 + CO_2 \leftrightharpoons CH_3OH + H_2O$$

$$2H_2 + CO \leftrightharpoons CH_3OH$$

Any methanol production technology may be used. Methanol is synthesised in a synthesis unit, which may comprise a methanol reactor containing a methanol synthesis catalyst. The process can be operated on a once-through basis or a recycle basis in which unreacted product gas, after optional methanol removal, is mixed with scrubbed second synthesis gas in the desired ratio and returned to the methanol synthesis reactor. The methanol synthesis, because it is exothermic, may involve cooling by indirect heat exchange surfaces in contact with the reacting gas, or by subdividing the catalyst bed and cooling the gas between the beds by injection of cooler gas or by indirect heat exchange. However, because the methanol synthesis unit is directed principally to making only sufficient formaldehyde for stabiliser production, in a preferred arrangement the methanol synthesis unit comprises a single once-through adiabatic methanol synthesis reactor containing a bed of methanol synthesis catalyst. This reduces the cost and complexity of the present invention compared to known methanol-ammonia co-production processes.

If desired, steam may be added to the scrubbed second synthesis gas, preferably after any heating step, to moderate or control the methanol synthesis reaction. The mole fraction of steam in the feed at the inlet of the methanol synthesis reactor may be up to the total mole fraction of carbon oxides ($CO+CO_2$) in the feed to the reactor.

A crude methanol product comprising methanol, water and trace amounts of impurities such as ethanol may be recovered by cooling of the product gas stream recovered from the methanol reactor to below the dew point, e.g. with cooling water. If desired, liquid ammonia may be used in a further cooling stage. Alternatively, or in addition, methanol may be recovered by scrubbing the product gas with water.

Any methanol synthesis catalyst may be used, but preferably it is based on a promoted or un-promoted copper/zinc oxide/alumina composition, for example those having a copper content in the range 50-70% wt, preferably 50-60% wt. Promoters include oxides of Mg, Cr, Mn, V, Ti, Zr, Ta, Mo, W, Si and rare earths. In the catalyst, the zinc oxide content may be in the range 20-90% wt, preferably 20-40% wt. The proportion of aluminium oxide in the catalyst is preferably in the range 5-15% wt. The one or more oxidic promoter compounds, if present, may be present in an amount in the range 0.01-10% wt. Magnesium compounds are preferred promoters and the catalyst preferably contains magnesium in an amount 1-5% wt, expressed as MgO. The synthesis gas may be passed over the catalyst at an inlet temperature to the catalyst in the range 200-320° C., and at a pressure in the range 20-250 bar abs, preferably 20-120 bar abs, and a space velocity in the range 500-20000 $h^{-1}$. Because the aim of the process is not to maximise methanol production, the inlet temperature of the methanol synthesis stage may be lower, e.g. 200-270° C. thus extending the catalyst lifetime by reducing sintering of the active copper sites.

In the present process, a single stage of methanol synthesis is sufficient. Nevertheless, if desired, the methanol synthesis may be part of a multiple stage synthesis process where the product gas, with or without condensate removal, is fed to one or more further methanol synthesis reactors, which may contain the same or different methanol synthesis catalyst. Such methanol production apparatus and catalysts are commercially available. A purge gas stream may be removed to prevent the undesirable build-up of inert/unreactive gases. If desired methanol may also be synthesised from this purge gas, or hydrogen recovered from it to adjust the stoichiometry of the feed gas or to generate power.

The unreacted gas stream recovered from the methanol synthesis unit after separation of a crude methanol stream is the methanol synthesis off-gas. It comprises nitrogen, hydrogen, and small amounts of methane, argon, carbon monoxide and carbon dioxide. In order to utilise the hydrogen contained within it in ammonia synthesis, the methanol synthesis off-gas is fed, optionally with additional steam, to a shifted gas stream. Thus the methanol synthesis off-gas may be combined, with or without heating, with a partially- or fully-shifted gas recovered from a high temperature shift stage. Alternatively, the methanol synthesis off-gas may be passed, without heating, to a shifted gas recovered from a stage of isothermal shift, medium temperature shift or low temperature shift stage, downstream of a high temperature shift stage. Preferably the methanol synthesis off-gas is fed from the methanol synthesis unit, without cooling, to a shifted gas upstream of a cooling step.

The crude methanol stream recovered from the methanol synthesis unit contains water and other impurities that are often separated from the product methanol by one or more stages of distillation. In the present process, preferably all of the recovered methanol is oxidised to produce formaldehyde. The formaldehyde stabiliser production unit may use purified methanol as the feed or a crude methanol as the feed. By "crude methanol" we include the direct product of the methanol synthesis reactor and a methanol product in which the water content has been adjusted to the range 5-20% by weight so that the formaldehyde stabiliser products are produced efficiently at suitable concentrations. This makes it possible to send crude methanol directly to the formaldehyde plant without the need for multiple distillation steps. Using crude methanol saves both capital cost on distillation columns and associated equipment, as well as the operating cost of this equipment, resulting in a significant benefit.

The crude methanol may be sent for storage in a suitable storage tank. Alternatively, the crude methanol may be subjected to one or more purification stages, including a de-gassing stage in a methanol purification unit prior to feeding it to the oxidation reactor. The de-gassing stage or any distillation stages may be provided by distillation columns heated using heat recovered from the oxidation reactor or elsewhere in the process. In particular, the degassing stage may be heated using steam generated by the oxidation stage. This simplification of the purification offers significant savings in capital and operating costs for the process.

Methanol is oxidised with air to produce formaldehyde in the formaldehyde stabiliser production unit. Any formaldehyde production technology using air as the oxidant may be used. The formaldehyde stabiliser production unit may comprise an oxidation reactor containing an oxidation catalyst. The oxidation catalyst may be provided as a fixed bed or within externally-cooled tubes disposed within the reactor. A compressed air source, which may be from the single source as described above, is used in the formaldehyde stabiliser production unit. The air may be in the temperature range 10-50° C. The air and methanol may be passed to the reactor containing an oxidation catalyst in which the methanol is oxidised. Air is preferably provided at 1.1-5 bar abs, e.g. from a first stage of compression of the air fed to the process. The amount of air fed to the formaldehyde stabiliser production unit is a relatively small proportion of the air fed to the overall process and so compression costs are not significantly increased and may be more than compensated for by the removal of additional compression equipment.

Production of formaldehyde from methanol and oxygen may be performed either in a silver- or a metal oxide-catalysed process operated at methanol-rich or methanol-lean conditions, respectively. Hence the oxidation catalyst may be selected from either a silver catalyst or a metal oxide catalyst, preferably comprising a mixture of iron and molybdenum oxides.

Vanadium oxide catalysts may also be used. In the metal oxide process, the principal reaction is the oxidation of the methanol to formaldehyde;

$$2CH_3OH+O_2 \rightarrow 2CH_2O+2H_2O$$

Over silver catalysts, in addition to the above oxidation reaction, methanol is also dehydrogenated in the principal reaction for this type of catalyst;

$$CH_3OH \rightarrow CH_2O + H_2$$

In the metal oxide process, formaldehyde is produced in multi-tube reactors. Typically, a reactor comprises 10-30,000 tubes containing catalyst pellets or extrudates and cooled by oil or by molten salts as heat transfer fluid. Since the reaction is highly exothermic ($\Delta N=-156$ kJ/mol), isothermal conditions are difficult to obtain and consequently a hotspot may be formed within the reaction zone. In order to limit the hot spot temperature, at the first part of the reactor the catalyst can be diluted with inert pellets or extrudates. The catalyst used in the oxide process is preferably a mixture of iron molybdate $Fe_2(MoO_4)_3$ and molybdenum trioxide $MoO_3$ with a Mo:Fe atomic ratio between 2 and 3. The plant yield is high (88-94%) and neither molybdenum nor iron are toxic, which is favourable considering both environmental and human health aspects.

Air is preferably used at levels to maintain the oxygen content at the inlet of the reactor below the explosive limit. The feed gas may therefore comprise 6.5 vol % methanol for a once-through reactor or about 8-11 vol % methanol where there is recirculation. The oxidation reactor may be operated adiabatically or isothermally, where the heat of reaction can be used to generate steam. The inlet temperature to the oxidation reactor is typically in the range 80-270° C., with iron-based catalytic processes operating up to 400° C. and silver-based processes up to 650° C.

A single passage through the oxidation reactor can result in high yields of formaldehyde, or if desired it is possible to recycle unreacted gases, which comprise mainly of nitrogen, to the reactor inlet to maintain a low oxygen concentration. Due to the scale required in the present process, the formaldehyde production stage may be operated without recycle of oxidised gas to the inlet of the oxidation reactor as this removes the need for a recycle compressor and hence offers further savings.

An absorption tower may be used to extract the formaldehyde product from the oxidised gas mixture into either water to produce aqueous formaldehyde solution, or a urea solution to produce a urea-formaldehyde concentrate (UFC). The absorption tower may contain a selection of packing, trays and other features to promote the absorption, and cooling water may be used to provide the product at a temperature in the range 20-100° C. The absorption stage typically runs at a slightly lower pressure than the reactor.

In step (h) of the process, products made from the formaldehyde are used to stabilise urea. The formaldehyde stabiliser production unit may be used to produce an aqueous formaldehyde solution (formalin) or a urea-formaldehyde concentrate (UFC). Both substances may be used as stabilisers. Urea formaldehyde concentrate that may be used typically comprises a mixture of about 60% wt formaldehyde, about 25% wt urea and the balance about 15% water. Such a product may be termed "UFC85". Other UFC products may also be used, e.g. UFC80. Other formaldehyde products may also be produced. Excess formaldehyde products may be recovered and sold.

The formaldehyde stabiliser production unit generates a vent gas which may be passed to a vent gas treatment unit such as an emission control unit or emission control system (ECS) and discharged to atmosphere. An emission control unit or system may comprise a catalytic combustor that reacts any carbon monoxide, methanol, formaldehyde and dimethyl ether in the vent gas with oxygen. The gas emitted from an ECS, i.e. an ECS effluent, may comprise carbon dioxide, steam and nitrogen and therefore may be recycled, preferably after suitable compression, to one or more stages of the process. Thus the ECS effluent may be passed to the carbon dioxide-removal stage where steam and carbon dioxide may be recovered, to provide additional nitrogen in the synthesis gas. Alternatively, the ECS effluent may be provided to the methanol synthesis stage where the carbon dioxide may be reacted with hydrogen in the synthesis gas to produce additional methanol. Alternatively, the ECS effluent may be fed to the urea production unit to provide carbon dioxide for additional urea production.

In another embodiment, the vent gas treatment unit comprises a gas-liquid separator that separates the nitrogen-rich off-gas from liquid methanol, which may be recycled to the oxidation reactor directly or after one or more stages of purification. The nitrogen-rich gas separated in the separator may be compressed and passed to the ammonia synthesis stage.

Alternatively, the formaldehyde vent gas may be recycled directly to the process, i.e. the vent gas treatment unit or system may be omitted. In one embodiment, the formaldehyde vent gas is recycled directly to the synthesis gas generation unit as a fuel gas so that the organic contaminants present in the vent gas may be combusted to generate energy. The formaldehyde vent gas may, for example, be recycled directly to the fuel gas stream of a primary reformer or may be fed to a furnace for steam generation. In this way, an ECS or vent gas treatment unit is not required, which offer considerable savings. Alternatively, the vent gas may be combined with a hydrocarbon feedstock fed to the synthesis gas generation unit.

Alternatively, the formaldehyde vent gas may be recycled directly to the carbon dioxide removal stage so that the carbon dioxide and water vapour present in the vent gas may be captured. Organic contaminants such as methanol, formaldehyde and dimethyl ether may also be captured, e.g. using a PSA unit.

Alternatively, the formaldehyde vent gas may be recycled directly to the methanol synthesis stage. Direct recycling is simpler and is preferred. With direct recycling, the by-products will be limited by equilibrium across the methanol synthesis catalyst and so will not accumulate in this recycle loop. The nitrogen is also recovered without the need for catalytic combustion or intensive pressurisation.

The formaldehyde vent gas may be recycled directly to one, two or more of these alternatives.

The formaldehyde stabiliser production unit may also produce an aqueous waste stream, for example a condensate recovered as a by-product of the methanol oxidation. This condensate may contain organic compounds such as methanol, formaldehyde and dimethyl ether and therefore provide a potential source of hydrocarbon for the process. In one embodiment, the process condensate is recycled to the synthesis gas generation stage where it is used to generate steam for use in steam reforming. The steam may be formed in a conventional boiler and added to the hydrocarbon feed or may, be generated in a saturator to which the aqueous effluent and hydrocarbon are fed. Alternatively, the effluent may be fed to a process condensate stripper.

The process by using the parallel methanol synthesis as described is able to operate with smaller and so less-expensive equipment that the prior art processes. Moreover, the pressure drop through the scrubber methanol synthesis unit can be configured to match that through the water gas shift stages so that no re-compression of the methanol synthesis off-gas is required. This offers a distinct advantage over the prior art processes.

The present process is particularly suitable for retro-fitting to an existing urea production facility because it requires few changes to the existing arrangement of unit operations and can have a minimal impact on the ammonia/urea production rate. Such retro-fitting, often termed revamping, can also provide additional flexibility in methanol and formaldehyde production and usefully provides a local source of stabiliser for the urea production unit. Accordingly, the invention further provides a method for revamping a urea production facility, said facility comprising a synthesis gas generation unit, one or more water-gas shift reactors, a condensate removal unit, a carbon dioxide removal unit, a methanation unit, an ammonia synthesis unit, a urea synthesis unit and a urea stabilisation unit, by steps comprising installing (1) means for recovering a synthesis gas stream from the synthesis gas generation unit, (2) a scrubber for removing contaminants from the recovered synthesis gas stream, (3) a methanol synthesis unit for synthesising methanol from the scrubbed synthesis gas, (4) means for recovering methanol and a methanol synthesis off-gas, (5) means for feeding the methanol synthesis off-gas to a shifted gas produced by the one or more water-gas shift reactors, (6) a formaldehyde stabiliser production unit for converting the methanol into a stabiliser prepared using formaldehyde, and (7) means for feeding at least a portion of the stabiliser to the urea stabilisation unit.

The present invention will now be described by reference to the accompanying drawings in which FIG. 1 is a schematic representation of a process according to one aspect of the present invention.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

In FIG. 1, a natural gas stream 10, steam 12 and an air stream 14 are fed to a synthesis gas generation unit 18 comprising a primary reformer and secondary reformer. The natural gas is primary reformed with steam in externally-heated catalyst filled tubes in the primary reformer and the primary reformed gas subjected to secondary reforming in the secondary reformer with the air to generate a synthesis gas comprising nitrogen, hydrogen, carbon dioxide, carbon monoxide and steam. A flue gas 16 is discharged from the primary reformer. A synthesis gas stream 20 is recovered from the synthesis gas generation unit 18 and divided into a first synthesis gas stream 22 and a second synthesis gas stream 24.

The first synthesis gas stream 22 is subjected to water-gas shift in a high temperature shift reactor 26 containing a high temperature shift catalyst to form a partially shifted gas and then, following a cooling step, in a low temperature shift reactor 28 containing a low temperature shift catalyst to form a shifted gas. The water-gas shift reaction increases the hydrogen and carbon dioxide contents and the steam and carbon monoxide contents are decreased. The shifted gas is cooled in heat exchange with cold water to below the dew point and a condensate 31 removed by a separator 30. A dried shifted gas is fed from the separator 30 to a carbon dioxide removal unit 32 operating by means of absorption. A carbon dioxide and water stream is recovered from the removal unit 32 by line 34 for further use. A carbon dioxide-depleted synthesis gas 36 comprising hydrogen, carbon monoxide and nitrogen is passed from the carbon dioxide removal unit 32 to a methanation unit 38 comprising a methanator vessel containing a bed of methanation catalyst. Carbon oxides remaining in the synthesis gas 36 are converted to methane and water in the methanation reactor. Water is recovered from the methanation unit 38 by line 40. The methanated off-gas is an ammonia synthesis gas comprising principally nitrogen and hydrogen with a small amount of methane. The ammonia synthesis gas is passed from the methanation unit 38 by line 42 to an ammonia synthesis unit 44 comprising an ammonia converter containing one or more beds of ammonia synthesis catalyst. The ammonia converter is operated in a loop with a portion of the reacted gas fed to the inlet of the converter. Ammonia is produced in the converter and recovered from the ammonia synthesis unit 44 by line 46. A purge gas stream 48 comprising methane and unreacted hydrogen and nitrogen is recovered from the ammonia synthesis unit 44 and provided to the synthesis gas generation unit 18 as fuel and/or feed to the primary and/or secondary reformers. A vent gas stream 50 is also recovered from the ammonia synthesis unit 44. A portion 52 of the ammonia is separated from the product stream 46. The remaining ammonia is passed to a urea synthesis unit 54 where it is reacted with a purified carbon dioxide stream provided by stream 34 to produce a urea stream and water. Water is recovered from the urea synthesis unit 54 by line 56. The urea stream is passed from the urea synthesis unit 54 by line 58 to a stabilisation unit 60 comprising a stabilisation vessel where it is treated with aqueous formaldehyde or a urea formaldehyde concentrate provided by line 62 to form a stabilised urea product. The stabilised urea product is recovered from the stabilisation unit 60 by line 64.

The second synthesis gas stream 24 is cooled in a heat exchanger, condensate is optionally separated, and the gas fed to a scrubber unit 66 fed with a purified water/condensate stream 68. The scrubber removes contaminants such as ammonia present in the synthesis gas and produces a scrubber liquor 70 which may be treated and recycled. The scrubbed synthesis gas is then heated and fed via line 72 to a methanol synthesis unit 74. Methanol is synthesised in a single adiabatic methanol synthesis reactor containing a copper-based methanol synthesis catalyst on a once-through basis. The product gas recovered from the reactor is cooled to condense methanol and water which is separated as crude methanol from the unreacted gases by a separator 76. Crude methanol is recovered from the separator 76, de-gassed, and fed via line 78 to a formaldehyde stabiliser production unit 80 comprising a methanol oxidation reactor containing an oxidation catalyst. An air source 82 is fed to the oxidation reactor where it is reacted with the methanol to produce formaldehyde. The oxidation reactor is operated in a loop with a portion of the reacted gas fed to the inlet of the reactor. The formaldehyde stabiliser production unit is fed with cooling water 84 and generates a steam stream 86 and a formaldehyde vent gas 88. The formaldehyde is recovered in an absorption tower which may either be fed with water or urea provided via line 90 such that either an aqueous formaldehyde or a urea-formaldehyde concentrate (UFC) stabiliser product stream 62 may be recovered from the production unit 80 for further use. A portion of the stabiliser product stream 62 can be taken for use in, for example, a separate urea-stabilisation plant or for sale, if the flow of formaldehyde produced is in excess of that required for the associated urea plant.

A methanol synthesis off-gas stream 92 comprising hydrogen, nitrogen and unreacted carbon monoxide recovered from the separator 76 is passed, optionally with additional steam, to the shifted gas downstream of the high-temperature shift reactor 26 and upstream of the low-temperature shift reactor 28.

Whereas in FIG. 1, the second portion 24 of synthesis gas is taken after secondary reforming, it may also be recovered from the primary reformed gas. Furthermore, although the methanol synthesis off-gas 92 is shown being combined with the shifted gas downstream of the high-temperature shift reactor 26, it may alternatively be combined with a shifted gas recovered from the low temperature shift reactor 28. Furthermore, the air streams 14 and 82 may be obtained from a single compressed source. Furthermore, the contaminated scrubber liquor 70 may be combined with the condensate 31 recovered from separator 30 and purified to form at least part of the purified water stream 68. The other water and condensate streams, 40, 56, 86 may if desired also be combined and purified. Furthermore, the vent gas 88 from the formaldehyde stabiliser production unit may be recycled to the process upstream of the methanator, e.g. to the synthesis gas generation unit or synthesis gas itself.

The present invention will now be described with reference to the following example.

A process according to FIG. 1 was modelled and compared with a process described in WO2016/132091 A1. The process according to FIG. 1 was configured to have the second synthesis gas stream 24 comprising 9.9% volume of the synthesis gas 20. The methanol synthesis unit then produced 23.3 tonnes/day methanol which was converted into 33.8 tonnes/day of UFC-85, which was used to stabilise urea. The methanol synthesis off-gas was combined with the partially shifted gas from the high temperature shift reactor 26 and the combined stream processed to produce 2181.8 tonnes/day ammonia.

In comparison, the process of WO2016/132091 A1 had a higher associated pressure drop relative to throughput. Thus, for the same methanol and formaldehyde requirement, and the same inlet pressure to the ammonia synthesis gas compression, 2.5% vol more flow inlet the ammonia plant was possible. This corresponded to an increase in hydrogen supplied to the ammonia synthesis unit of 0.8% vol and a potential increase of ammonia production of 16.4 tonnes/day based on the same loop efficiency.

The invention claimed is:

1. A process for producing formaldehyde-stabilised urea, comprising the steps of:
    (a) generating a synthesis gas comprising hydrogen, nitrogen, carbon monoxide, carbon dioxide and steam in a synthesis gas generation unit;
    (b) dividing the synthesis gas into a first synthesis gas stream and a smaller second synthesis gas stream;
    (c) subjecting the first synthesis gas stream to one or more stages of water-gas shift in one or more water-gas shift reactors to form a shifted gas;
    (d) cooling the shifted gas to below the dew point and recovering condensate to form a dried shifted gas;
    (e) recovering carbon dioxide from the dried shifted gas in a carbon dioxide removal unit to form a carbon dioxide-depleted synthesis gas;
    (f) subjecting the carbon dioxide-depleted synthesis gas to a stage of methanation in one or more methanation reactors to form an ammonia synthesis gas;
    (g) synthesising ammonia from the ammonia synthesis gas in an ammonia production unit and recovering the ammonia;
    (h) reacting a portion of the ammonia and at least a portion of the recovered carbon dioxide stream in a urea production unit to form a urea stream; and
    (i) stabilising urea in the urea stream by mixing the urea stream and a stabiliser prepared using formaldehyde to form a stabilised urea, wherein the formaldehyde is generated by steps comprising;
        (1) passing the second portion of synthesis gas through a scrubber to remove contaminants therefrom and form a scrubbed synthesis gas;
        (2) synthesising methanol from the scrubbed synthesis gas in a methanol synthesis unit, and recovering the methanol and a methanol synthesis off-gas;
        (3) combining the methanol synthesis off-gas with the shifted gas; and
        (4) subjecting at least a portion of the recovered methanol to oxidation with air in a formaldehyde stabiliser production unit to produce formaldehyde.

2. The process of claim 1, wherein the synthesis gas generation stage comprises primary reforming in a fired or gas-heated steam reformer and secondary reforming in a secondary reformer with air or oxygen-enriched air.

3. The process of claim 2, wherein the second synthesis gas stream is recovered from a primary reformed gas stream or a secondary reformed gas stream.

4. The process of claim 1, wherein the second synthesis gas stream consists of a portion of a secondary reformed gas.

5. The process of claim 1, wherein the second synthesis gas stream is in a range of from 0.25 to 30% by volume of the synthesis gas.

6. The process of claim 1, wherein the stage of water-gas shift comprises a stage of high temperature shift in a high temperature shift reactor.

7. The process of claim 1, wherein the water-gas shift stage comprises a high temperature shift stage to form a partially shifted gas and a low temperature shift stage to form a shifted gas mixture.

8. The process of claim 1, wherein the second synthesis gas stream, before it is passed to the scrubber, is cooled to below the dew point so that steam present in the second synthesis gas condenses as water, which is removed by a separator, to provide a dried second synthesis gas stream gas.

9. The process of claim 1, wherein the scrubber is fed with a demineralised water and/or a purified condensate.

10. The process of claim 1, wherein a contaminated scrubber liquor recovered from the scrubber is combined with the condensate recovered from the shifted gas.

11. The process of claim 1, wherein the scrubbed second synthesis gas is heated to a methanol synthesis inlet temperature in the range of from 200-320° C.

12. The process of claim 11, wherein the scrubbed second synthesis gas is heated in a heating step by a gas-gas interchanger that recovers heat from the second synthesis gas stream.

13. The process according to of claim 1, wherein steam is added to the scrubbed second synthesis gas.

14. The process of claim 1, wherein the methanol synthesis is operated on a once-through basis, using a single adiabatic methanol synthesis reactor containing a bed of methanol synthesis catalyst.

15. The process of claim 6, wherein the methanol synthesis off-gas is fed with or without heating to a shifted gas recovered from a stage of high temperature shift.

16. The process of claim 6, wherein the methanol synthesis off-gas is fed, without heating, to a shifted gas after a stage of isothermal shift, medium temperature shift or low temperature shift.

17. A method for revamping a urea production facility, to provide a process of claim 1, wherein said facility comprises a synthesis gas generation unit, one or more water-gas shift reactors, a condensate removal unit, a carbon dioxide removal unit, a methanation unit, an ammonia synthesis unit, a urea synthesis unit and a urea stabilisation unit, by steps comprising installing:
(1) means for recovering a synthesis gas stream from the synthesis gas generation unit,
(2) a scrubber for removing contaminants from the recovered synthesis gas stream,
(3) a methanol synthesis unit for synthesising methanol from the scrubbed synthesis gas,
(4) means for recovering methanol and a methanol synthesis off-gas,
(5) means for feeding the methanol synthesis off-gas to a shifted gas produced by the one or more water-gas shift reactors,
(6) a formaldehyde stabiliser production unit for converting the methanol into a stabiliser prepared using formaldehyde, and
(7) means for feeding at least a portion of the stabiliser to the urea stabilisation unit.

18. The process of claim 1, wherein the second synthesis gas stream is in a range of from 0.25 to 20% by volume of the synthesis gas.

19. The process of claim 1, wherein the second synthesis gas stream is in a range of from 0.25 to 10% by volume, of the synthesis gas.

20. The process of claim 1, wherein the scrubbed second synthesis gas is heated to a methanol synthesis inlet temperature in the range of from 200 to 270° C.

\* \* \* \* \*